US010117970B2

(12) United States Patent
Michal et al.

(10) Patent No.: US 10,117,970 B2
(45) Date of Patent: Nov. 6, 2018

(54) LOCAL DELIVERY OF WATER-SOLUBLE OR WATER-INSOLUBLE THERAPEUTIC AGENTS TO THE SURFACE OF BODY LUMENS

(71) Applicant: The Spectranetics Corporation, Colorado Springs, CO (US)

(72) Inventors: Eugene T. Michal, San Francisco, CA (US); Matthew J. Pollman, San Francisco, CA (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 15/471,579

(22) Filed: Mar. 28, 2017

(65) Prior Publication Data

US 2017/0224875 A1    Aug. 10, 2017

Related U.S. Application Data

(60) Continuation of application No. 14/852,790, filed on Sep. 14, 2015, now Pat. No. 9,603,973, which is a
(Continued)

(51) Int. Cl.
| | |
|---|---|
| *A61K 31/337* | (2006.01) |
| *A61L 29/08* | (2006.01) |
| *A61L 29/14* | (2006.01) |
| *A61L 29/16* | (2006.01) |
| *A61M 25/10* | (2013.01) |

(52) U.S. Cl.
CPC .......... *A61L 29/085* (2013.01); *A61K 31/337* (2013.01); *A61L 29/148* (2013.01); *A61L 29/16* (2013.01); *A61M 25/10* (2013.01); *A61M 25/1027* (2013.01); *A61L 2300/416* (2013.01);
(Continued)

(58) Field of Classification Search
None
See application file for complete search history.

(56) References Cited

U.S. PATENT DOCUMENTS

| | | | |
|---|---|---|---|
| 4,010,259 A | 3/1977 | Johansson | |
| 4,589,873 A | 5/1986 | Schwartz et al. | |

(Continued)

FOREIGN PATENT DOCUMENTS

| | | |
|---|---|---|
| EA | 012091 B1 | 8/2009 |
| EP | 0681475 A1 | 11/1995 |

(Continued)

OTHER PUBLICATIONS

Russian Office Action, and English language translation, issued in Russial Appl. No. 2014145442 dated Feb. 15, 2016.
(Continued)

*Primary Examiner* — Aradhana Sasan

(57) ABSTRACT

A method and device for local delivery of a water-insoluble therapeutic agent to the tissue of a normal or diseased body lumen is disclosed. An expandable structure of a medical disposable device, such as a balloon of a balloon catheter, is coated with a non-durable coating which comprises poly (HEMA) complexed with iodine and has a substantially water-insoluble therapeutic agent dispersed therein. The medical disposable device is inserted into a body lumen, and expanded to contact the non-durable coating against the body lumen and deliver the substantially water-insoluble therapeutic agent to the body lumen tissue.

12 Claims, 3 Drawing Sheets

Related U.S. Application Data continuation of application No. 14/254,160, filed on Apr. 16, 2014, now Pat. No. 9,132,211, which is a continuation of application No. 13/919,443, filed on Jun. 17, 2013, now Pat. No. 8,734,825, which is a continuation of application No. 13/310,326, filed on Dec. 2, 2011, now Pat. No. 8,491,925, which is a division of application No. 12/726,101, filed on Mar. 17, 2010, now Pat. No. 8,114,429, which is a continuation-in-part of application No. 12/712,134, filed on Feb. 24, 2010, now Pat. No. 8,128,951, which is a continuation-in-part of application No. 12/558,420, filed on Sep. 11, 2009, now Pat. No. 9,198,968, which is a continuation-in-part of application No. 12/210,344, filed on Sep. 15, 2008, now Pat. No. 8,257,722.

(52) U.S. Cl.
CPC .... *A61L 2420/06* (2013.01); *A61M 2025/105* (2013.01); *A61M 2025/1075* (2013.01)

(56) References Cited

U.S. PATENT DOCUMENTS

| | | |
|---|---|---|
| 4,847,324 A | 7/1989 | Creasy |
| 4,950,256 A | 8/1990 | Luther et al. |
| 5,001,009 A | 3/1991 | Whitbourne |
| 5,256,701 A | 10/1993 | Tamura et al. |
| 5,302,392 A | 4/1994 | Karakelle et al. |
| 5,302,394 A | 4/1994 | Beahm |
| 5,304,121 A | 4/1994 | Sahatjian |
| 5,331,027 A | 7/1994 | Whitbourne |
| 5,464,650 A | 11/1995 | Berg et al. |
| 5,525,348 A | 6/1996 | Whitbourne et al. |
| 5,616,608 A | 4/1997 | Kinsella et al. |
| 5,662,609 A | 9/1997 | Slepian |
| 5,674,192 A | 10/1997 | Sahatjian et al. |
| 5,733,888 A | 3/1998 | Carver et al. |
| 5,733,925 A | 3/1998 | Kunz et al. |
| 5,762,638 A | 6/1998 | Shikani et al. |
| 5,788,979 A | 8/1998 | Alt et al. |
| 5,811,447 A | 9/1998 | Kunz et al. |
| 5,824,049 A | 10/1998 | Ragheb et al. |
| 5,886,026 A | 3/1999 | Hunter et al. |
| 5,900,246 A | 5/1999 | Lambert |
| 5,954,706 A | 9/1999 | Sahatjian |
| 5,972,992 A | 10/1999 | Carver et al. |
| 5,977,164 A | 11/1999 | Carver et al. |
| 6,074,659 A | 6/2000 | Kunz et al. |
| 6,096,070 A | 8/2000 | Ragheb et al. |
| 6,096,331 A | 8/2000 | Desai et al. |
| 6,110,483 A | 8/2000 | Whitbourne et al. |
| 6,120,784 A | 9/2000 | Snyder, Jr. |
| 6,146,358 A | 11/2000 | Rowe |
| 6,156,373 A | 12/2000 | Zhong et al. |
| 6,179,817 B1 | 1/2001 | Zhong |
| 6,218,016 B1 | 4/2001 | Tedeschi et al. |
| 6,268,390 B1 | 7/2001 | Kunz |
| 6,299,604 B1 | 10/2001 | Ragheb et al. |
| 6,306,166 B1 | 10/2001 | Barry et al. |
| 6,306,421 B1 | 10/2001 | Kunz et al. |
| 6,369,039 B1 | 4/2002 | Palasis et al. |
| 6,403,635 B1 | 6/2002 | Kinsella et al. |
| 6,419,692 B1 | 7/2002 | Yang et al. |
| 6,429,232 B1 | 8/2002 | Kinsella et al. |
| 6,506,408 B1 | 1/2003 | Palasis |
| 6,506,411 B2 | 1/2003 | Hunter et al. |
| 6,515,009 B1 | 2/2003 | Kunz et al. |
| 6,537,579 B1 | 3/2003 | Desai et al. |
| 6,544,544 B2 | 4/2003 | Hunter et al. |
| 6,638,767 B2 | 10/2003 | Unger et al. |
| 6,638,797 B2 | 10/2003 | Noguchi et al. |
| 6,663,881 B2 | 12/2003 | Kunz et al. |
| 6,673,053 B2 | 1/2004 | Wang et al. |
| 6,730,064 B2 | 5/2004 | Ragheb et al. |
| 6,753,071 B1 | 6/2004 | Pacetti |
| 6,774,278 B1 | 8/2004 | Ragheb et al. |
| 6,835,387 B2 | 12/2004 | Herrmann |
| 6,846,815 B2 | 1/2005 | Myers et al. |
| 6,855,770 B2 | 2/2005 | Pinchuk et al. |
| 6,918,927 B2 | 7/2005 | Bates et al. |
| 6,926,919 B1 | 8/2005 | Hossainy et al. |
| 7,008,979 B2 | 3/2006 | Schottman et al. |
| 7,105,175 B2 | 9/2006 | Schwarz |
| 7,179,251 B2 | 2/2007 | Palasis |
| 7,279,174 B2 | 10/2007 | Pacetti et al. |
| 7,291,165 B2 | 11/2007 | Rosenthal et al. |
| 7,381,418 B2 | 6/2008 | Richard |
| 7,407,507 B2 | 8/2008 | Maeda et al. |
| 7,445,792 B2 | 11/2008 | Toner et al. |
| 7,541,047 B2 | 6/2009 | Rogasch et al. |
| 7,750,041 B2 | 7/2010 | Speck et al. |
| 7,803,149 B2 | 9/2010 | Bates et al. |
| 7,811,622 B2 | 10/2010 | Bates et al. |
| 7,875,284 B2 | 1/2011 | Reyes et al. |
| 7,914,806 B2 | 3/2011 | Strickler et al. |
| 7,919,108 B2 | 4/2011 | Reyes et al. |
| 8,021,678 B2 | 9/2011 | Hossainy et al. |
| 8,114,429 B2 | 2/2012 | Michal et al. |
| 8,128,951 B2 | 3/2012 | Michal et al. |
| 8,147,540 B2 | 4/2012 | Reyes et al. |
| 8,257,305 B2 | 9/2012 | Speck et al. |
| 8,257,722 B2 | 9/2012 | Michal et al. |
| 8,313,521 B2 | 11/2012 | Ruane et al. |
| 8,389,043 B2 | 3/2013 | Speck et al. |
| 8,439,868 B2 | 5/2013 | Speck et al. |
| 8,491,925 B2 | 7/2013 | Michal et al. |
| 8,563,023 B2 | 10/2013 | Michal et al. |
| 8,734,825 B2 | 5/2014 | Michal et al. |
| 9,132,211 B2 | 9/2015 | Michal et al. |
| 9,198,968 B2 | 12/2015 | Michal et al. |
| 9,603,973 B2 | 3/2017 | Michal et al. |
| 2002/0151844 A1 | 10/2002 | Yang et al. |
| 2003/0052424 A1 | 3/2003 | Turner et al. |
| 2003/0059454 A1 | 3/2003 | Barry et al. |
| 2003/0203991 A1 | 10/2003 | Schottman et al. |
| 2003/0225451 A1 | 12/2003 | Sundar |
| 2004/0073284 A1 | 4/2004 | Bates et al. |
| 2004/0117006 A1 | 6/2004 | Lewis et al. |
| 2004/0117007 A1 | 6/2004 | Whitbourne et al. |
| 2004/0175406 A1 | 9/2004 | Schwarz |
| 2004/0241094 A1 | 12/2004 | Chung et al. |
| 2005/0004661 A1 | 1/2005 | Lewis et al. |
| 2005/0036946 A1 | 2/2005 | Pathak et al. |
| 2005/0059965 A1 | 3/2005 | Eberl et al. |
| 2005/0147690 A1 | 7/2005 | Masters et al. |
| 2005/0159704 A1 | 7/2005 | Scott et al. |
| 2005/0226903 A1 | 10/2005 | Rogasch et al. |
| 2005/0250672 A9 | 11/2005 | Speck et al. |
| 2005/0278021 A1 | 12/2005 | Bates et al. |
| 2006/0020243 A1 | 1/2006 | Speck et al. |
| 2006/0020331 A1 | 1/2006 | Bates et al. |
| 2006/0034769 A1 | 2/2006 | Kohn et al. |
| 2006/0212106 A1 | 9/2006 | Weber et al. |
| 2006/0228453 A1 | 10/2006 | Cromack et al. |
| 2006/0240070 A1 | 10/2006 | Cromack et al. |
| 2007/0065481 A1 | 3/2007 | Chudzik et al. |
| 2007/0065482 A1 | 3/2007 | Chudzik et al. |
| 2007/0065483 A1 | 3/2007 | Chudzik et al. |
| 2007/0065484 A1 | 3/2007 | Chudzik et al. |
| 2007/0071792 A1 | 3/2007 | Varner et al. |
| 2007/0078446 A1 | 4/2007 | Lavelle |
| 2007/0104766 A1 | 5/2007 | Wang et al. |
| 2007/0190103 A1 | 8/2007 | Hossainy et al. |
| 2008/0020013 A1 | 1/2008 | Reyes et al. |
| 2008/0021385 A1 | 1/2008 | Barry et al. |
| 2008/0051871 A1 | 2/2008 | Tuch |
| 2008/0078400 A1 | 4/2008 | Martens et al. |
| 2008/0102033 A1 | 5/2008 | Speck et al. |
| 2008/0102034 A1 | 5/2008 | Speck et al. |
| 2008/0113035 A1 | 5/2008 | Hunter |
| 2008/0118543 A1 | 5/2008 | Pacetti et al. |
| 2008/0118544 A1 | 5/2008 | Wang |

(56) References Cited

U.S. PATENT DOCUMENTS

| | | |
|---|---|---|
| 2008/0124372 A1 | 5/2008 | Hossainy et al. |
| 2008/0132992 A1 | 6/2008 | Bates et al. |
| 2008/0140002 A1 | 6/2008 | Ramzipoor et al. |
| 2008/0145396 A1 | 6/2008 | Bates et al. |
| 2008/0146489 A1 | 6/2008 | Pacetti et al. |
| 2008/0153900 A1 | 6/2008 | Hunter |
| 2008/0175887 A1 | 7/2008 | Wang |
| 2008/0311173 A1 | 12/2008 | Schwarz et al. |
| 2009/0054837 A1 | 2/2009 | Von Holst et al. |
| 2009/0074707 A1 | 3/2009 | Rogasch et al. |
| 2009/0098176 A1 | 4/2009 | Helmus et al. |
| 2009/0112239 A1 | 4/2009 | To |
| 2009/0136560 A1 | 5/2009 | Bates et al. |
| 2009/0186414 A1 | 7/2009 | Srivastava et al. |
| 2009/0196931 A1 | 8/2009 | Kunz et al. |
| 2009/0216317 A1 | 8/2009 | Cromack et al. |
| 2009/0218731 A1 | 9/2009 | Rogasch et al. |
| 2009/0227948 A1 | 9/2009 | Chen et al. |
| 2009/0227949 A1 | 9/2009 | Knapp et al. |
| 2009/0285974 A1 | 11/2009 | Kerrigan et al. |
| 2009/0297584 A1 | 12/2009 | Lim et al. |
| 2010/0015200 A1 | 1/2010 | McClain et al. |
| 2010/0030183 A1 | 2/2010 | Toner et al. |
| 2010/0063570 A1 | 3/2010 | Pacetti et al. |
| 2010/0063585 A1 | 3/2010 | Hoffmann et al. |
| 2010/0068170 A1 | 3/2010 | Michal et al. |
| 2010/0137975 A1 | 6/2010 | Wittchow |
| 2010/0198190 A1 | 8/2010 | Michal et al. |
| 2010/0278744 A1 | 11/2010 | Speck et al. |
| 2011/0015664 A1 | 1/2011 | Kangas et al. |
| 2011/0015725 A1 | 1/2011 | Bates et al. |
| 2011/0070355 A1 | 3/2011 | Bavaro et al. |
| 2011/0143014 A1 | 6/2011 | Stankus et al. |
| 2011/0144577 A1 | 6/2011 | Stankus et al. |
| 2011/0196340 A1 | 8/2011 | Barry et al. |
| 2011/0295200 A1 | 12/2011 | Speck et al. |
| 2012/0064141 A1 | 3/2012 | Andreacchi et al. |
| 2012/0064223 A1 | 3/2012 | Gamez et al. |
| 2012/0078228 A1 | 3/2012 | Michal et al. |
| 2012/0135133 A1 | 5/2012 | O'Neill et al. |
| 2012/0165922 A1 | 6/2012 | Gong et al. |
| 2012/0239001 A1 | 9/2012 | Barry et al. |
| 2012/0289933 A1 | 11/2012 | Michal et al. |
| 2013/0053947 A1 | 2/2013 | Kangas et al. |
| 2013/0129814 A1 | 5/2013 | Pacetti et al. |
| 2013/0189329 A1 | 7/2013 | Wang |
| 2013/0197436 A1 | 8/2013 | Wang |

FOREIGN PATENT DOCUMENTS

| | | |
|---|---|---|
| EP | 0706376 A1 | 4/1996 |
| EP | 0797988 A2 | 10/1997 |
| EP | 1011171 A2 | 6/2000 |
| EP | 1011743 A1 | 6/2000 |
| EP | 1118325 A2 | 7/2001 |
| EP | 1372737 A2 | 1/2004 |
| EP | 1539266 A1 | 6/2005 |
| EP | 1539267 A2 | 6/2005 |
| EP | 1632259 A2 | 3/2006 |
| EP | 1649853 A2 | 4/2006 |
| EP | 1666070 A1 | 6/2006 |
| EP | 1666071 A1 | 6/2006 |
| EP | 1666092 A2 | 6/2006 |
| EP | 1669092 A1 | 6/2006 |
| EP | 1857127 A1 | 11/2007 |
| EP | 1986711 A2 | 11/2008 |
| EP | 2004251 A2 | 12/2008 |
| EP | 2010244 A2 | 1/2009 |
| EP | 2193813 A2 | 6/2010 |
| EP | 2200674 A2 | 6/2010 |
| WO | 91/12779 A1 | 9/1991 |
| WO | 93/11120 A1 | 6/1993 |
| WO | 94/16706 A1 | 8/1994 |
| WO | 95/03036 A1 | 2/1995 |
| WO | 98/58988 A1 | 12/1998 |
| WO | 99/08729 A1 | 2/1999 |
| WO | 01/28589 A2 | 4/2001 |
| WO | 2004/028610 A2 | 4/2004 |
| WO | 2005004945 A2 | 1/2005 |
| WO | 2005044506 A1 | 5/2005 |
| WO | 2006/022754 A2 | 3/2006 |
| WO | 2007/035865 A1 | 3/2007 |
| WO | 2007/094940 A2 | 8/2007 |
| WO | 2007106441 A2 | 9/2007 |
| WO | 2007/111885 A2 | 10/2007 |
| WO | 2007/112006 A2 | 10/2007 |
| WO | 2007143159 A2 | 12/2007 |
| WO | 2008003298 A2 | 1/2008 |
| WO | 2008/031596 A1 | 3/2008 |
| WO | 2008/104573 A2 | 9/2008 |
| WO | 2009/036014 A2 | 3/2009 |
| WO | 2009/124570 A1 | 10/2009 |
| WO | 2009158276 A2 | 12/2009 |
| WO | 2010/030995 A2 | 3/2010 |
| WO | 2010036537 A2 | 4/2010 |

OTHER PUBLICATIONS

Chinese Office Action from Appl. No. 201080064497.3 dated Nov. 3, 2014.

Official Action issued in Japanese Application No. 2012-554976 dated Apr. 2, 2014.

Examiner's First Report issued in Australian Application No. 2013280330 dated Dec. 24, 2014.

Official Action issued in Japanese Application No. 2012-554976 dated Jan. 8, 2015.

International Search Report from PCT Application No. PCT/US2013/048052 dated Sep. 6, 2013.

U.S. Appl. No. 12/121,692, filed May 15, 2008, Kerrigan.

Gray, William A., et al., "Drug-Coated Balloons for the Prevention of Vascular Restenosis" Circulation: Journal of the American Heart Association, vol. 121, pp. 2672-2680, accessibleathttp://circ.ahajournals.org/cgi/content/full/121/24/2672,American Heart Association, Dallas, TX Jun. 22, 2010.

Jones, David S., Poly(E-caprolactone) and poly(e-caprolactone)-polyvinylpyrrolidone-iodine blends as ureteral biomaterials: characterisation of mechanical and surface properties, degration and resistance to encrustation in vitro., Biomaterials, vol. 23, pp. 4449-4458, 2002.

Katsuda, S., et al., The Role of Cytoplasmic Microtubules in Regulation of Smooth Muscle Proliferation. International Atherosclerosis Society Poster Sessions, Abstract Book from 8.sup.th International Symposium on Atherosclerosis, Rome, Oct. 9-13, 1988, p. 446.

B. Braun Vascular Systems, "SeQuent.RTM. Please", Brochure Product No. 6050120, accessed Sep. 9, 2009 at http://www.deb-bbraun.com/doc/doc download.cfm?6736&uuid= 9E5F74B02A5AE6266471 CF5AF5F43933&&IRACER.sub.—Autolink&&, B. BraunMelsungenAGVascular Systems, 10 pages, Berlin, Germany.

Weaver, J.V.M., et al., "Stimulus Responsive Water-Soluble Polymers Based on 2-Hydroxyethyl Methacrylate" Macromolecules, vol. 37 (7), pp. 2395-2403, Mar. 2004.

Consigny, P. Macke et al., "Local Delivery of an Antiproliferative Drug with Use of Hydrogel-coated Angioplasty Balloons!", Journal of Vascular and Interventional Radiology, vol. 5, No. 4, pp. 554-560, Jul.-Aug. 1994.

Sollott "Taxol Inhibits Neointimal Smooth Muscle Cell Accumulation after Angioplasty in the Rat", The Journal of Clinical Investigation, Inc., vol. 95, pp. 1869-1876, Apr. 1995.

CV Ingenuity Office Action for U.S. Appl. No. 12/210,344 dated Nov. 23, 2010.

CV Ingenuity Office Action for U.S. Appl. No. 12/210,344 dated Apr. 19, 2011.

CV Ingenuity Office Action for U.S. Appl. No. 12/210,344 dated Jun. 24, 2011.

CV Ingenuity Office Action for U.S. Appl. No. 12/210,344 dated Nov. 7, 2011.

(56) References Cited

OTHER PUBLICATIONS

CV Ingenuity Office Action for U.S. Appl. No. 12/712,134 dated Mar. 31, 2011.
CV Ingenuity Notice of Allowance for U.S. Appl. No. 12/712,134 dated Oct. 3, 2011.
CV Ingenuity Office Action for U.S. Appl. No. 12/726,101 dated Mar. 30, 2011.
CV Ingenuity Notice of Allowance for U.S. Appl. No. 12/726,101 dated Sep. 29, 2011.
PCT International Preliminary Report on Patentability for International Application No. PCT/US2010/027731, dated Aug. 28, 2012, 8 pages.
PCT Invitation to Pay Additional Fees for International Application No. PCT/US2009/056842, dated Dec. 17, 2009, 8 pages.
PCT International Search Report and Written Opinion for International Application No. PCT/US2009/056842, dated Mar. 31, 2010, 17 pages.
PCT International Search Report and Written Opinion for International Application No. PCT/US2010/027731, dated Mar. 21, 2011, 11 pages.
CV Ingenuity Office Action for U.S. Appl. No. 12/210,344 dated Mar. 19, 2012.
CV Ingenuity Notice of Allowance for U.S. Appl. No. 12/210,344 dated Jun. 12, 2012.
U.S. Appl. No. 12/121,692, filed May 15, 2008, Kerrigan, Cameron K.
Jones, David S., Poly(.epsilon.-caprolactone) and poly-(.epsilon.-caprolactone)-polyvinylpyrrolidone-iodine blends as ureteral biomaterials: characterisation of mechanical and surface properties, degration and resistance to encrustationinvitro.,Biomaterials, vol. 23, pp. 4449-4458, 2002.
B. Braun Vascular Systems, "SeQuent.RTM. Please", Product Brochure No. 6050120, accessed Sep. 9, 2009 at http://www.deb-bbraun.com/doc/doc.sub.---download.cfm?6736&uuid=9E5F74B02A--5AE6266471CF5AF5F43933&&IRACER.sub.—Autolink&&, B. BraunMelsungenAGVascular Systems, 10 pages, Berlin, Germany.
Canadian Office Action from Appl. No. CA 2,877,656 dated Feb. 4, 2016.
European Examination Report issued in Appl. No. EP 09792515.0 dated May 11, 2017.
Japanese Office Action from Appl. No. JP 2015-520481 dated Oct. 26, 2015.
Canadian Office Action issued in Appl. No. CA 2,942,795 dated Oct. 26, 2017 (5 pages).

LOCAL DELIVERY OF WATER-SOLUBLE OR WATER-INSOLUBLE THERAPEUTIC AGENTS TO THE SURFACE OF BODY LUMENS

RELATED APPLICATIONS

This application is a continuation of U.S. application Ser. No. 14/852,790, filed Sep. 14, 2015, now U.S. Pat. No. 9,603,973, which is a continuation of U.S. application Ser. No. 14/254,160, filed Apr. 16, 2014, now U.S. Pat. No. 9,132,211, which is a continuation of U.S. application Ser. No. 13/919,443, filed Jun. 17, 2013, now U.S. Pat. No. 8,734,825, which is a continuation of U.S. patent application Ser. No. 13/310,326, filed Dec. 2, 2011, now U.S. Pat. No. 8,491,925, which is a divisional of U.S. patent application Ser. No. 12/726,101, filed Mar. 17, 2010, now U.S. Pat. No. 8,114,429, which is a continuation-in-part of U.S. patent application Ser. No. 12/712,134, filed Feb. 24, 2010, now U.S. Pat. No. 8,128,951, which is a continuation-in-part application of pending U.S. patent application Ser. No. 12/558,420, filed Sep. 11, 2009, which is a continuation-in-part application of U.S. patent application Ser. No. 12/210,344, filed Sep. 15, 2008, now U.S. Pat. No. 8,257,722, the full disclosures of each of which are incorporated herein by reference.

FIELD

Embodiments of the present invention relate to the field of medical therapeutic agent delivery. More particularly embodiments of this invention relate to methods and devices used for local delivery of water-soluble or water-insoluble therapeutic agents to the surface of normal or diseased body lumens.

BACKGROUND INFORMATION

Sporadic, inherited, environmental, and iatrogenic diseases associated with significant morbidity and mortality develop in the wall of endothelial cell-lined and epithelial cell-lined body lumens. For example, atherosclerosis and post-procedural restenosis develop in the arterial wall. Adenocarcinoma, esophageal varices, and cholangiocarcinoma develop in the gastrointestinal tract wall. The efficacy of systemic drug therapy for these diseases may be limited by inadequate drug delivery to the diseased tissue and/or dose limiting toxic effects in non-diseased tissue. Local delivery of drugs to diseased tissue in body lumen walls can overcome these limitations: therapeutic concentrations of drugs can be achieved without systemic toxicity.

SUMMARY

Embodiments of the present invention disclose a novel approach to coating an expandable structure of a medical disposable device, such as a balloon of a balloon catheter, which can be used for local therapeutic agent delivery to the surface of body lumens. The approach permits forming a coating with high levels of a therapeutic agent (e.g. paclitaxel) and utilizes a unique chemical formulation designed to permit forming a coating that provides a uniform therapeutic agent density across the balloon surface using a simple, reproducible and hence easily manufacturable application process. This novel coating process can be used to locally delivery a uniform dose of water-soluble and water-insoluble therapeutic agents to treat a variety of diseases that arise in body lumen walls. In addition, the novel coating approach may accommodate therapeutic levels of combinations of therapeutic agents (e.g. paclitaxel and dexamethasone acetate) directed at distinct therapeutic targets to increase the therapeutic efficiency of the procedure.

In an embodiment, a coating solution is single-dip coated on an expandable structure having an outer surface, such as an angioplasty balloon useful for either coronary or peripheral arteries of the vasculature, in order to form an amphiphilic polymer coating on the outer surface of the expandable structure. The coating solution may contain an amphiphilic polymer or co-polymer in majority or exclusively non-aqueous solvents, a therapeutic agent or combination of therapeutic agents (e.g. paclitaxel and dexamethasone acetate), and an optional plasticizer and/or wax. In an embodiment, the amphiphilic polymer or co-polymer is complexed with iodine, which is not covalently bound to the amphiphilic polymer or co-polymer. The coating solution may also contain a plurality of amphiphilic polymers or co-polymers. After coating, the balloon is dried and folded for delivery.

The coated medical disposable device may be used in a therapeutic operation. In an embodiment, the coated medical disposable device is inserted into a body lumen and expanded to contact the non-durable amphiphilic polymer coating against the body lumen. Hydration of the coating occurs immediately when exposed to aqueous fluids, such as blood in vivo, causing the non-durable amphiphilic polymer coating to dissolve and the therapeutic agent to release into tissue of the body lumen. In an embodiment, the significant or total solubility of the amphiphilic polymer or co-polymer in blood may prevent embolic hazards associated with the amphiphilic polymer coating, and allow for the coating to be quickly and uniformly removed from the medical disposable device during the therapeutic operation. Thus, the amphiphilic polymer coating is bioerodible in the sense that it is removable by bodily fluids, and non-durable. In an embodiment, at least 50%, by volume, of the amphiphilic polymer coating is removed from the device within 180 seconds of inflating in vivo. In an embodiment, at least 90% of the amphiphilic polymer coating is removed from the device within 300 seconds of inflating in vivo, and more preferably within 180 seconds or 90 seconds of inflating in vivo. Also, this active dissolution of the amphiphilic polymer coating may assist in the transfer of hydrophobic, substantially water-insoluble therapeutic agents such as paclitaxel from the device (e.g. balloon) to the tissue.

In accordance with embodiments of the invention, the amphiphilic polymer or co-polymer may be complexed with iodine. It is demonstrated that complexed iodine increases the solubility of water-insoluble therapeutic agents such as paclitaxel, rapamycin and everolimus in aqueous conditions. This suggests that the complexed iodine may additionally assist in tissue uptake of the water-insoluble therapeutic agents in vivo. In an embodiment, the dried amphiphilic polymer coating includes a therapeutic agent dispersed in a polymer matrix comprising at least one amphiphilic polymer or co-polymer complexed with iodine, an optional plasticizer and/or wax.

The amphiphilic polymer or co-polymer can be fully or partially amphiphilic. In an embodiment, a continuous aggregate polymer matrix of the coating is uniformly dissolvable and removable from an outer surface of an expandable structure of a catheter assembly in an aqueous solvent, and at least partially dissolvable in a non-aqueous solvent. Being significantly or fully dissolvable in aqueous solvents is advantageous in that total solubility in blood can prevent against embolic hazards associated with the amphiphilic polymer coating. Having at least partial solubility in non-aqueous solvents is advantageous in a coating process in which an amphiphilic polymer or co-polymer and water-insoluble therapeutic agent are dissolved in the same solution.

In an embodiment, the dried amphiphilic polymer coating comprises at least one amphiphilic polymer or co-polymer complexed with iodine and at least one amphiphilic polymer or co-polymer which is not complexed with iodine. In an embodiment, 25-100 wt % of the total amphiphilic polymer or co-polymer in the dried coating is complexed with iodine. For example, the dried coating may contain 0-75 wt % of an amphiphilic polymer which is not complexable with iodine and 25-100 wt % iodinated PVP as amphiphilic polymer components.

In an embodiment, the dried coating present on the balloon has an iodine to iodine complexable amphiphilic polymer and/or co-polymer weight ratio (I/P) of 1-30%, a therapeutic agent (drug) to polymer matrix weight ratio (D/P) from 25-100%, and a drug density of approximately 0.1-10.0 μg/mm$^2$. In an embodiment, the dried coating is present on a catheter balloon, the drug is paclitaxel, and the amphiphilic polymer is PVP. The dried coating has an iodine to PVP weight ratio (I/P) of 1-30%, a paclitaxel to polymer matrix weight ratio (D/P) from 25-100%, and a paclitaxel density of approximately 0.1-5.0 μg/mm$^2$.

DETAILED DESCRIPTION

Figure 1A:
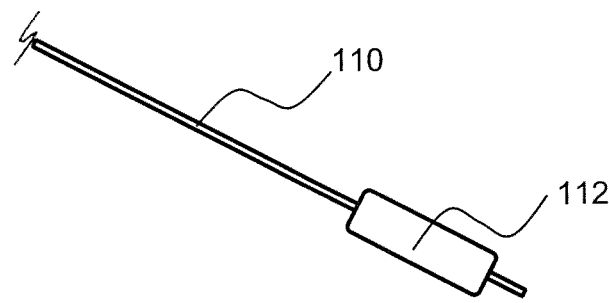
FIG. 1A is a side view illustration of a balloon catheter while the balloon is in the expanded position.

Embodiments of the present invention disclose methods and devices used for local delivery of water-soluble or water-insoluble therapeutic agents to the surface of normal or diseased body lumens.

Various embodiments described herein are described with reference to figures. However, certain embodiments may be practiced without one or more of these specific details, or in combination with other known methods and configurations. In the following description, numerous specific details are set forth, such as specific configurations, compositions, and processes, etc., in order to provide a thorough understanding of the present invention. In other instances, well-known processes and manufacturing techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the invention. Thus, the appearances of the phrase "in one embodiment" or "an embodiment" in various places throughout this specification are not necessarily referring to the same embodiment of the invention. Furthermore, the particular features, configurations, compositions, or characteristics may be combined in any suitable manner in one or more embodiments.

In one aspect, embodiments of the invention disclose a medical disposable device in which an amphiphilic polymer coating is disposed on the outer surface of an expandable structure. The amphiphilic polymer coating includes at least one therapeutic agent and at least one amphiphilic polymer or co-polymer. The amphiphilic polymer coating may optionally include additional components such as a plasticizer and/or wax. The therapeutic agent can be either water-soluble or water-insoluble. Hydration of the amphiphilic polymer coating occurs immediately when exposed to aqueous fluids such as blood in vivo causing the amphiphilic polymer coating to dissolve and the therapeutic agent to release into tissue of the body lumen. Thus, the amphiphilic polymer coating is bioerodible in the sense that it is removable by bodily fluids, and non-durable. In an embodiment, the significant or total solubility of the polymer or co-polymer in blood prevents embolic hazards associated with the amphiphilic polymer coating, and allows for the coating to be quickly and uniformly removed from the medical disposable device during the therapeutic operation.

In an embodiment, the medical disposable device is a catheter with an expandable balloon having an amphiphilic polymer coating comprising a therapeutic agent dispersed in the coating. The catheter is advanced within a body lumen to align the balloon with the target tissue, the balloon is expanded to 2-20 atmospheres to bring the amphiphilic polymer coating into contact with the target tissue, causing the amphiphilic polymer coating to dissolve and the therapeutic agent payload to release rapidly to the target tissue in vivo because the device will contact the target tissue for only a short amount of time, approximately 5 to 300 seconds. Because the device is to be used for only a short time period and then removed from the body, it is considered to be a "medical disposable" device rather than "implantable."

The term amphiphilic as used herein means at least partially dissolvable in aqueous solvents such as, but not limited to, blood in-vivo, as well as at least partially dissolvable in non-aqueous solvents such as, but not limited to, ethanol, methanol, and/or isopropanol. Accordingly, an "amphiphilic polymer coating" and "amphiphilic polymer or co-polymer" according to embodiments of the invention are at least partially dissolvable in both aqueous and non-aqueous solvents.

In some embodiments, the amphiphilic polymer or co-polymer is fully amphiphilic, meaning fully dissolvable in both aqueous and non-aqueous solvents. Being fully dissolvable in aqueous solvents is advantageous in that total solubility in blood can prevent against embolic hazards associated with the amphiphilic polymer coating, and allow for the coating to be quickly and uniformly removed from the medical disposable device during the therapeutic operation. Being fully dissolvable in non-aqueous solvents is advantageous in a coating process where an expandable structure may be dip coated into a non-aqueous coating solution in which the amphiphilic polymer or co-polymer and a water-insoluble therapeutic agent are dissolved.

In some embodiments, the amphiphilic polymer or co-polymer is not fully amphiphilic. For example, the amphiphilic polymer or co-polymer may exhibit significant or total solubility in aqueous solvents in order to prevent against embolic hazards associated with the amphiphilic polymer coating, and allow for the coating to be quickly and uniformly removed from the medical disposable device during the therapeutic operation. Also, the amphiphilic polymer or co-polymer may exhibit only partial solubility in non-aqueous solvents. In some instances, water may be added to a coating solution in order to dissolve the amphiphilic polymer or co-polymer. For example, a coating solution may be prepared in which the amphiphilic polymer or co-polymer and a water-insoluble therapeutic agent are dissolved in a mixture of aqueous and non-aqueous solvents. In an embodiment, the coating solution contains a majority of non-aqueous solvents. In an embodiment, the coating solution contains a ratio in the range of 100% to 80% non-aqueous solvent, and 0% to 20% aqueous solvent.

In an embodiment, additional components are included in the amphiphilic polymer coating that may not necessarily be dissolvable in both aqueous and non-aqueous solvents, yet the aggregate polymer matrix of the amphiphilic polymer coating is at least partially dissolvable in both aqueous and non-aqueous solvents. For example, embodiments of the invention may utilize water-soluble and/or water-insoluble therapeutic agents, as well as a water-insoluble wax or other components interdispersed in the aggregate polymer matrix of the amphiphilic polymer coating. In an embodiment, a minority weight percent of a hydrophobic polymer or co-polymer can be included in the polymer matrix of the amphiphilic polymer coating. For example, a small minority of hydrophobic polymer or co-polymer could be added to extend the lifetime of the coating in vivo or slightly retard the release rate of the therapeutic agent, while still allowing rapid and uniform dissolution of the coating in vivo.

In an embodiment, an amphiphilic polymer coating may include a substantially water-insoluble component dispersed within an amphiphilic polymer or co-polymer which is significantly or fully dissolvable in aqueous solvents but not fully soluble in non-aqueous solvents. In such an embodiment, the continuous aggregate polymer matrix of the coating is uniformly dissolvable and removable from a substrate in aqueous solvents (such as bovine serum, or blood in vivo), yet only partially dissolvable and removable from a substrate in non-aqueous solvents.

In an embodiment, an amphiphilic polymer coating may include a substantially water-insoluble component dispersed within an amphiphilic polymer or co-polymer which is fully dissolvable in both aqueous and non-aqueous solvents. In such an embodiment, the continuous aggregate polymer matrix of the coating is uniformly dissolvable and removable from a substrate in both aqueous solvents (such as bovine serum, or blood in vivo) and non-aqueous solvents. The particular solubility rate of the amphiphilic polymer coating may depend upon the particular solubility rate of the amphiphilic polymer(s) and/or co-polymer(s), and the inclusion of any additional ingredients such as plasticizers, waxes, hydrophobic polymers or co-polymers, etc. in the coating. In an embodiment, an amphiphilic polymer or co-polymer is selected which has a sufficiently high solubility rate in aqueous solutions in order to be utilized in a touch and go procedure where the coating is exposed to bodily fluids for only a short amount of time. In an embodiment, an amphiphilic polymer or co-polymer is selected which can be dissolved in a non-aqueous coating solution or an aqueous/non-aqueous coating solution in which a substantially water-insoluble therapeutic agent is also dissolved.

Amphiphilic Polymers or Co-Polymers

In one aspect, embodiments of the invention disclose an amphiphilic polymer coating including one or more amphiphilic polymers or co-polymers. In an embodiment, the amphiphilic polymer or co-polymer is a non-ionic thermoplastic polymer or co-polymer. In an embodiment, the amphiphilic polymer is hydroxypropyl cellulose (HPC), polyvinyl pyrrolidone (PVP), polyethylene glycol (PEG), methyl cellulose, hydroxypropyl methylcellulose, or co-polymers of N-vinylpyrrolidone with other reactive double bond containing monomers such as styrene, acrylic acid, vinyl acetate or vinyl caprolactam. PVP and HPC exhibit higher solubility rates in aqueous solvents than PEG. Molecular weight of the polymers may also factor into solubility rates. In an embodiment, the PEG has as molecular weight of 1.5 KD to 50 KD.

The amphiphilic polymer may also be a poly(hydroxyethyl methacrylic) acid, also known as poly(HEMA). In an embodiment, the poly(HEMA) has a number average molecular weight, Mn, below approximately 8 KD. In an embodiment, the poly(HEMA) has a number average molecular weight, Mn, of approximately 7 KD. In an embodiment, the amphiphilic polymer may be a co-polymer of HEMA with a monomer such as, but not limited to, glycidyl methacrylate (GMA) or acrylic acid. Co-polymers can be block or random.

The HEMA monomer in accordance with embodiments of the present invention is partially or fully soluble in water and lower alcohols, however, when the polymer is made by traditional synthesis methods such as free radical polymerization or anionic polymerization the polymer swells in water but is insoluble. This property is useful for soft contact lenses, which swell and soften in contact with water but do not dissolve in the eye, but is not suitable as a coating for rapidly releasing hydrophobic therapeutic agents into tissue where dissolution and erosion of the polymer is desired to achieve the rapid release.

An alternative synthesis method is described by J. V. M. Weaver et al. (Macromolecules 2004, 37, 2395-2403) in which a poly(HEMA) is synthesized by atom transfer radical polymerization (ATRP) using a morpholine based initiator (termed ME-Br). The authors determined that using the disclosed synthesis method the resultant poly(HEMA) had a molecular weight based solubility response in water, where polymers with a number average molecular weight, Mn, below approximately 8 KD had water solubility. Those with Mn between 10 KD and 14 KD displayed inverse temperature solubility, with cloud points increasing with the degree of polymerization, and those above approximately 15 KD were insoluble in water at any temperature.

In accordance with some embodiments of the present invention, a modification of the procedure used by J. V. M. Weaver et al. is disclosed, as described in Examples 10 and 11. In such embodiments, the synthesized poly(HEMA) at 10 KD and 7 KD were found to exhibit similar solubility to those disclosed by J. V. M. Weaver et al. The 10 K poly(HEMA) was found to be water insoluble, while the 7 KD poly(HEMA) was found to be water soluble. In an embodiment the 7 KD poly(HEMA) is suitable for use as an amphiphilic polymer.

In an embodiment, the amphiphilic polymer or co-polymer is complexed with iodine and the iodine is not covalently bonded to the amphiphilic polymer or co-polymer. For example, PVP, PEG, HPC and poly(HEMA) may be complexed with iodine, and it is expected that other suitable polymers such as methyl cellulose, hydroxypropyl methylcellulose, and co-polymers of N-vinylpyrrolidone with other reactive double bond containing monomers such as styrene, acrylic acid, vinyl acetate or vinyl caprolactam may also be complexed with iodine. In an embodiment, the poly(HEMA) complexed with iodine has a number average molecular weight, Mn, below approximately 8 KD, for example 7 KD. In an embodiment, the PEG complexed with iodine has as molecular weight of 1.5 KD to 50 KD. PVP complexed with iodine is also known as povidone iodine. Surprisingly, as suggested by the results of Table I and Table II, complexing a non-ionic amphiphilic polymer with iodine may increase solubility of a water-insoluble therapeutic agent such as paclitaxel, rapamycin and everolimus in vivo and therefore assist in tissue uptake of the water-insoluble therapeutic agent. This can reduce the time requirements of the medical procedure and amount of mechanical pressure and/or metabolic insufficiencies caused by sustained inflation of the expandable structure. In an embodiment, the amount of iodine complexed with the iodine complexable amphiphilic polymer and/or co-polymer in the coating is 1 to 30 weight % of the dry iodine complexable amphiphilic polymer and/or co-polymer weight.

In an embodiment, the dried coating comprises at least one amphiphilic polymer or co-polymer complexed with iodine and at least one amphiphilic polymer or co-polymer which is not complexed with iodine. In an embodiment, 25-100 wt % of the total amphiphilic polymer or co-polymers in the dried coating are complexed with iodine. For example, 25-100 wt % of the total amphiphilic polymer and/or co-polymer in the polymer matrix may be povidone iodine.

Complexing with iodine can also serve addition functions. It imparts an amber hue on the amphiphilic polymer coating, aiding in visualization outside of the body, and with the coating process. Additionally, as iodine has a large nuclear radius, it will provide radiopacity under fluoroscopy; the expandable structure will be visible under fluoro, and the dissolution of the amphiphilic polymer coating can be monitored as a function of time.

In an embodiment, the amphiphilic polymer or co-polymer is an ionic thermoplastic co-polymer or co-polymer. For example, the amphiphilic polymer or co-polymer can be poly (methyl vinyl ether-alt-maleic acid monobutyl ester) (available under the trade name Gantrez ES-425, from International Specialty Products (ISP), Wayne, N.J.) or poly (methyl vinyl ether-alt-maleic acid monoethyl ester) (available under the trade name Gantrez ES-225, from International Specialty Products (ISP), Wayne, N.J.).

In an embodiment, the amphiphilic polymer(s) or co-polymer(s) is fully amphiphilic. HPC (non-iodinated), iodinated HPC, PVP (non-iodinated) iodinated PVP (povidone iodine), PEG (non-iodinated), iodinated PEG, poly(HEMA) (non-iodinated) Mn below approximately 8 KD, iodinated poly(HEMA) Mn below approximately 8 KD, poly (methyl vinyl ether-alt-maleic acid monobutyl ester), and poly (methyl vinyl ether-alt-maleic acid monoethyl ester) are soluble in lower alcohols without the use of any water, which provides for a low surface tension and rapid evaporation. As used herein, the term "lower alcohols" means an alcohol having 4 carbon atoms or less. They are also freely soluble in water resulting in rapid dissolution in vivo. In an embodiment, this is beneficial when it is desired that the therapeutic agent transfer take place within 90 to 300 seconds of inflation. When the above amphiphilic polymers or co-polymers are dissolved in sufficient ethanol, alone or in combination, they are also freely miscible with acetone.

In an embodiment, where the therapeutic agent includes paclitaxel, this can be beneficial because paclitaxel is highly soluble in a mixture of a lower alcohol (e.g. ethanol, 2-propanol, n-butanol) and warm acetone, and the solvent combination enables a high drug loading.

In another embodiment, the amphiphilic polymer(s) or co-polymer(s) may not be fully amphiphilic. For example, methyl cellulose and hydroxypropyl methylcellulose are not fully soluble in non-aqueous solvent, however some grades are soluble in a solution which contains approximately 10% water and 90% non-aqueous solvent. It is also expected that other suitable co-polymers such as N-vinylpyrrolidone with other reactive double bond containing monomers such as styrene, acrylic acid, vinyl acetate or vinyl caprolactam may not be fully soluble in non-aqueous solvent, but may be soluble in solutions containing a ratio in the range of 100% to 80% non-aqueous solvent, and 0% to 20% aqueous solvent.

In an embodiment, the amphiphilic polymer coating may optionally include a plasticizer in the polymer matrix. A plasticizer may be particularly useful to increase the ductility and prevent the coating from cracking or delaminating while bending or folding in the dry state. Suitable plasticizers include, but are not limited to, propylene glycol, triethyl citrate, glycerol, and dibutyl sebacate. In an embodiment, the amphiphilic polymer is PVP-based (iodinated or non-iodinated) and the plasticizer is present at 30% to 85% by weight of the PVP. In an embodiment, the amphiphilic polymer is HPC-based (iodinated or non-iodinated) and the plasticizer is present at 5% to 15% by weight of the HPC. In an embodiment, the plasticizer may also be an at least partially amphiphilic polymer. For example, PEG having a molecular weight below 10 K Daltons is a suitable plasticizer. In an embodiment, the plasticizer is PEG 400.

In an embodiment, the amphiphilic polymer coating may optionally include a wax in the polymer matrix. A wax-like surface assists with the gliding quality of the amphiphilic polymer coating in relation with a body lumen surface and/or in relation with an optional protective sheath over the amphiphilic polymer coating. Suitable waxes include, but are not limited to bees wax, carnauba wax, polypropylene glycol, polydimethyl siloxane (PDMS), and PDMS derivatives.

In an embodiment, the amphiphilic polymer coating may optionally include a small minority of hydrophobic polymer or co-polymer in the polymer matrix to slightly extend the lifetime of the coating in vivo or slightly retard the release rate of the therapeutic agent, while still allowing rapid and uniform dissolution of the coating in vivo.

In an embodiment, a continuous aggregate polymer matrix of the coating is uniformly dissolvable and removable from the outer surface of the expandable structure in an aqueous solvent, and at least partially dissolvable in a non-aqueous solvent. Such a coating may be suitable for application in touch and go procedures where the therapeutic agent transfer takes place within, for example, 90 to 300 seconds. In an embodiment, the coating is dissolvable in bovine serum such that 90%, by volume, of the coating is removed within 300 seconds of soaking in bovine serum at 37° C., and more preferably within 90 seconds. For example, such dissolution can be accomplished when utilizing iodinated or non-iodinated PVP or HPC. In an embodiment, the coating is dissolvable in bovine serum such that 50%, by volume, of the coating is removed within 180 seconds of soaking in bovine serum at 37° C. For example, such an embodiment can be accomplished when utilizing iodinated or non-iodinated PVP, HPC or PEG (MW 1.5 KD to 50 KD).

In an embodiment, the coating is dissolvable in bovine serum such that 90%, by volume, of the coating is removed within 180 seconds of soaking in bovine serum at 37° C. For example, such an embodiment can be accomplished when utilizing iodinated or non-iodinated poly(HEMA) Mn 7 KD. It is expected that other iodinated or non-iodinated polymers such as methyl cellulose, hydroxypropyl methylcellulose, and co-polymers of N-vinylpyrrolidone with other reactive double bond containing monomers such as styrene, acrylic acid, vinyl acetate or vinyl caprolactam, as well as poly (methyl vinyl ether-alt-maleic acid monobutyl ester), and poly (methyl vinyl ether-alt-maleic acid monoethyl ester) should also exhibit suitable solubility rates for application in touch and go procedures where the therapeutic agent transfer takes place within, for example, 90 to 300 seconds.

Therapeutic Agents

In another aspect, embodiments of the invention disclose an apparatus and method for delivering therapeutic agents to treat a variety of diseases that arise in body lumen walls. The therapeutic agents useful in accordance with the present invention may be used singly or in combination. The therapeutic agents may be non-aqueous soluble (i.e. solvent soluble) and/or aqueous soluble. In an embodiment, the dried coating has a therapeutic agent (drug) to polymer matrix weight ratio (D/P) from 25-100%. As used herein the D in the D/P ratio includes all of the drugs in the coating unless the D/P ratio is utilized differently to specifically represent a single drug in the coating. As used herein the P in the D/P ratio includes all of the amphiphilic polymer and/or co-polymer(s), and additional components such as plasticizer and wax dispersed or otherwise uniformly integrated into the polymer matrix. The D/P may depend upon the molecular weight of the amphiphilic polymer and/or co-polymer, and presence of additional components such as a plasticizer and/or wax. D/P ratios higher than 100% may result longer dissolution times in vivo, thereby providing less efficient drug delivery during a treatment operation where a delivery balloon is inflated for 300 seconds or less. Additionally, D/P ratios higher than 100% may increase the likelihood of particulate generation, particularly for water-insoluble drugs. D/P ratios below 25% may require excessive coating thickness to achieve the required therapeutic agent loading on the medical disposable device. In an embodiment, the D/P ratio is 35-60%.

In an embodiment, the dried coating has a therapeutic agent (drug) density of approximately 0.1-10.0 μg/mm². The drug density may vary depending upon factors such as the specific drug and polymer matrix selections. In an embodiment, the dried coating is present on a catheter balloon, the drug is paclitaxel, and the amphiphilic polymer is PVP, and the dried coating has a paclitaxel density of approximately 0.1-3.0 μg/mm².

In an embodiment, non-aqueous soluble and/or water-insoluble therapeutic agents are particularly useful as components in a coating composition which includes a majority or exclusively non-aqueous solvents. For example, a non-aqueous soluble anti-proliferative agent such as paclitaxel may be used in combination with another therapeutic agent such as the anti-inflammatory agent dexamethasone. In an embodiment, therapeutic agents which may be, singly or in combination, locally delivered to the surface of normal or diseased body lumens can be classified into the categories of anti-proliferative agents, anti-platelet agents, anti-inflammatory agents, anti-thrombotic agents, and thrombolytic agents. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of non-aqueous soluble vinca alkaloids include, but are not limited to, paclitaxel (including the alkaloid itself and naturally occurring forms and derivatives thereof, as well as synthetic and semi-synthetic forms thereof), vincristine, etoposide, indirubin, and anthracycline derivatives, such as, for example, daunorubicin, daunomycin, and plicamycin. Other sub-classes of anti-mitotic agents include anti-mitotic alkylating agents, such as, for example non-aqueous soluble fotemustine, and anti-mitotic metabolites, such as, for example, non-aqueous soluble azathioprine, mycophenolic acid, leflunomide, teriflunomide, fluorouracil, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Examples of non-aqueous soluble anti-inflammatory agents that can also be used include, but are not limited to, dexamethasone, prednisone, hydrocortisone, estradiol, triamcinolone, mometasone, fluticasone, clobetasol, and non-steroidal anti-inflammatories, such as, for example, acetaminophen, ibuprofen, and sulindac. The arachidonate metabolite prostacyclin or prostacyclin analogs are examples of a vasoactive antiproliferative.

Therapeutic agents with pleiotropic effects on cell proliferation, immunomodulation and inflammation may also be used. Examples of such non-aqueous soluble agents include, but are not limited to the macrolides and derivatives thereof such as sirolimus (e.g. rapamycin), tacrolimus, everolimus, temsirolimus.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Non-aqueous soluble anti-platelet agents that act as inhibitors of adhesion of platelets include, but are not limited to, and tirofiban and RGD (Arg-Gly-Asp)-based peptides (Pegylated) that inhibit binding to gpIIbIIIa or .alpha.v.beta.3, compounds that block P-selectin or E-selectin binding to their respective ligands. Agents that inhibit ADP-mediated platelet aggregation include, but are not limited to, cilostazol.

Anti-thrombotic agents include chemical and biological entities that can intervene at any stage in the coagulation pathway. Examples of specific non-aqueous soluble entities include, but are not limited to, small molecules that inhibit the activity of factor Xa. Also included are direct thrombin inhibitors, such as, for example, argatroban, inogatran.

Other non-aqueous soluble therapeutic agents that can be used are cytotoxic drugs, such as, for example, apoptosis inducers, and topoisomerase inhibitors, including, irinotecan, and doxorubicin, and drugs that modulate cell differentiation such as inhibitors of histone deacetylase, including valproic acid.

Other non-aqueous soluble therapeutic agents that can be used include anti-lipaedemic agents, including but not limited to fenofibrate, clofibrate, and rosiglitazone and matrix metalloproteinase inhibitors, such as, for example, batimistat, antagonists of the endothelin-A receptor, such as, for example, darusentan.

In another embodiment, aqueous soluble therapeutic agents may be used. Aqueous soluble anti-mitotic agents include Epothilone A, Epothilone B and Epothilone D, and all other Epothilones. Aqueous soluble anti-platelet agents include RGD (Arg-Gly-Asp)-based peptides that inhibit binding to gpIIbIIIa or .alpha.v.beta.3. Aqueous soluble anti-thrombotic agents include heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Aqueous soluble thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase. Additional aqueous soluble therapeutic agents include recombinant antibodies for anti-platelet and anti-endothelin applications.

When used in the above or other treatments, a therapeutically effective amount of one of the non-aqueous soluble or aqueous soluble therapeutic agents in embodiments of the invention may be employed in pure form or, where such forms exist, in pharmaceutically acceptable salt, ester or prodrug form. Alternatively, the therapeutic agent may be administered as a pharmaceutical composition including the compound of interest in combination with one or more pharmaceutically acceptable excipients. As used herein, the phrase "therapeutically effective amount" of the therapeutic agents of the invention means a sufficient amount of the therapeutic agents to treat disorders, at a reasonable benefit/risk ratio applicable to any medical treatment. It will be understood, however, that the total daily usage of the therapeutic agents and compositions of embodiments of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the therapeutic agent at levels lower than required to achieve the desired therapeutic effect and to gradually increase the dosage until the desired effect is achieved.

Coating Process

Figure 1B:
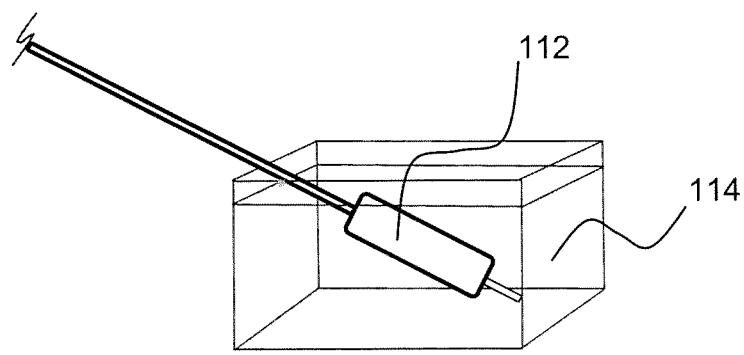
FIG. 1B is an isometric view illustration of a balloon catheter dipped in a coating solution while the balloon is in the expanded position.
Figure 1C:
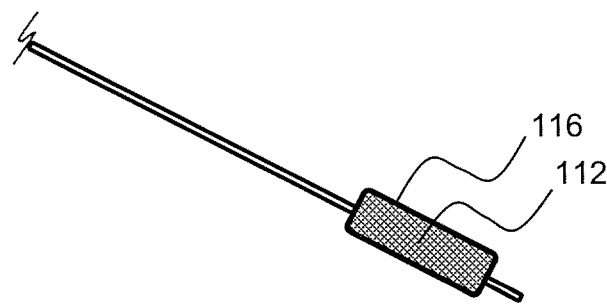
FIG. 1C is a side view illustration of a balloon catheter with a coated balloon surface.

The amphiphilic polymer coating containing a therapeutic agent or agents and an amphiphilic polymer or co-polymer can be formed from with a variety of techniques including deposition, spray coating, and dip coating. FIG. 1A-FIG. 1C are illustrations of a particular embodiment in which the amphiphilic polymer coating is formed by dip coating the expandable structure of a medical disposable device, such as the balloon of a balloon catheter, into a coating solution or coating mixture. Utilizing embodiments of the invention, the dip coating process can provide a uniform therapeutic agent density across the balloon surface using a simple and reproducible single-dip, thereby eliminating the need for multiple dips to load the therapeutic agent into the coating.

FIG. 1A is an illustration of a balloon catheter 110 with an uncoated balloon 112 in the expanded position (e.g. inflated) . As shown in FIG. 1B, the uncoated expanded balloon 112 can be dipped into a coating solution or mixture 114 and then extracted from coating solution 114 at a rate of 0.05 to 0.4 in/min. As described above, the coating solution 114 may include aqueous or more preferably non-aqueous solvents, an amphiphilic polymer or co-polymer, and a therapeutic agent. The coating solution 114 may optionally include additional components such as a plasticizer and/or wax.

In an embodiment, the coating solution 114 viscosity is at least 5 cps and less than approximately 75 cps. After dipping the expanded balloon 112 into the coating solution 114, the expanded balloon 112 is then removed from the coating solution, as shown in FIG. 1C resulting in a uniform coating 116 on the expanded balloon 112. In an embodiment, optionally a gas (e.g. argon, oxygen) plasma may be used on the catheter prior to coating to enhance the coating adhesion.

In an embodiment, the use of an amphiphilic polymer or co-polymer and non-aqueous soluble therapeutic agent enables the use of non-aqueous solvents to dissolve the polymer or co-polymer and therapeutic agent. In alternate embodiments, where the therapeutic agent and/or amphiphilic polymer or co-polymer is not fully soluble in non-aqueous solutions, an aqueous solution or a solution including a mixture of aqueous and non-aqueous solvents may be used. A majority or exclusively non-aqueous solvents in the coating solution provides rapid evaporation, a lower surface tension, and improved substrate wetting compared to an aqueous solution, which aids in obtaining coating uniformity. In an embodiment, a suitable solution may contain a ratio in the range of 100% to 80% non-aqueous solvent, and 0% to 20% aqueous solvent. For example, solvents with boiling points lower than water can be used singly or in combination in the coating solution 114, such as ethanol, methanol, or methyl ethyl ketone, isopropanol (2-propanol), and/or butanol that rapidly evaporate in ambient conditions, which consequently reduces gravity induced surface defects such as sagging. Dip coating into a coating solution with majority or exclusively non-aqueous solvents permits forming a coating with high levels of a therapeutic agent, and permits forming a coating that provides a uniform therapeutic agent density across the balloon surface using a simple, reproducible and hence easily manufacturable application process. For example, when HPC (non-iodinated), iodinated HPC, PVP (non-iodinated), iodinated PVP (povidone iodine), PEG (non-iodinated), iodinated PEG, poly(HEMA) (non-iodinated) Mn below approximately 8 KD, iodinated poly(HEMA) Mn below approximately 8 KD, poly (methyl vinyl ether-alt-maleic acid monobutyl ester), and poly (methyl vinyl ether-alt-maleic acid monoethyl ester) are dissolved in sufficient ethanol, they are also freely miscible with acetone. In an embodiment, where the therapeutic agent includes paclitaxel, this can be beneficial because paclitaxel is highly soluble in a mixture of a lower alcohol (e.g. ethanol, 2-propanol, n-butanol) and acetone, and the solvent combination enables a high drug loading. In an embodiment, the therapeutic agent is rapamycin or everolimus. In an embodiment including methyl cellulose, hydroxypropyl methylcellulose, and/or co-polymers of N-vinylpyrrolidone with other reactive double bond containing monomers such as styrene, acrylic acid, vinyl acetate or vinyl caprolactam, the solution may contain water up to a ratio of 80/20 non-aqueous to aqueous solvents.

The coating solution 114 may be prepared by mixing the therapeutic agent, solvent(s), polymer(s) and other components such as plasticizer into a single container. Several mixing and/or dissolving operations may be also performed prior to combining multiple solutions to form the coating solution 114. For example, where an amphiphilic polymer or co-polymer is complexed with iodine, a complexed polymer solution may be prepared. For example, $I_2$ may be dissolved in alcohol (or a solution having a ratio of up to 80/20 non-aqueous and aqueous solvents), then dry polymer powder is added to the $I_2$ and alcohol. Agitation and/or heat may be applied to the solution to dissolve the polymer. For example, 0.05 grams of $I_2$ is dissolved in 12 grams of 2-propanol. Then 1.00 grams of PVP (360 KD, ISP) is added. The suspension is shaken continuously until the PVP is dissolved, about 1 hour. In an embodiment, the resulting solution is a 20% povidone-iodine in 2-propanol solution.

The therapeutic agent can then be dissolved in a separate alcohol, alcohol and acetone solution, or a solution having a ratio of up to 80/20 non-aqueous and aqueous solvents. For example, 0.1 grams paclitaxel is dissolved in 0.1 grams ethanol and 0.18 grams of 50% PEG-400 in acetone at 40° C. This solution can then be cooled to room temperature and added to 0.55 grams of the 20% povidone-iodine in 2-propanol solution. In an embodiment, the combined coating solution has a drug (i.e. paclitaxel) to polymer matrix (i.e. iodinated-PVP and PEG-400) ratio (D/P) of 50%, the solution is 31.8% non-volatile, and the drug (i.e. paclitaxel) is 33% of the non-volatile. After coating, the balloon is dried, deflated and folded for delivery. In an embodiment, after the balloon is dried, but before deflating and folding for delivery, the balloon may optionally be dip coated into a separate coating solution containing a wax to form a thin wax coating (not shown) over the amphiphilic polymer coating, rather than incorporating the wax into the amphiphilic polymer coating.

Local Therapeutic Agent Delivery Process

Figure 2A:
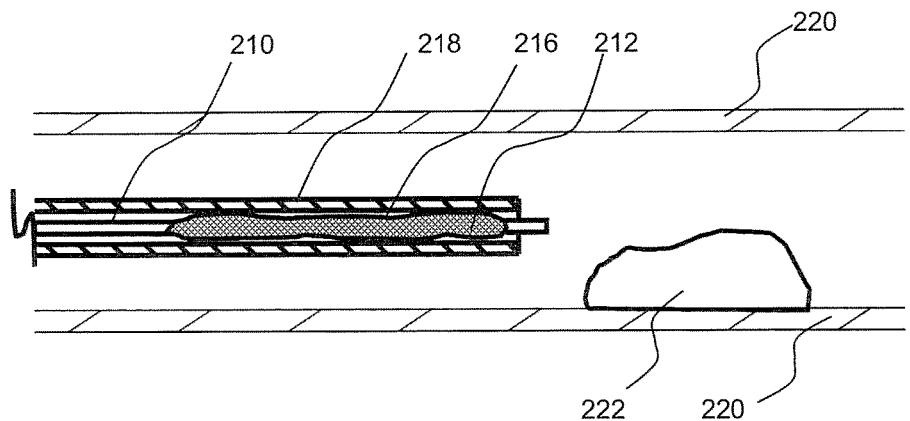
FIG. 2A is a side view illustration of an amphiphilic polymer coating disposed on an outer surface of unexpanded balloon of a balloon catheter covered by a retractable sheath and inserted into a body lumen.
Figure 2B:
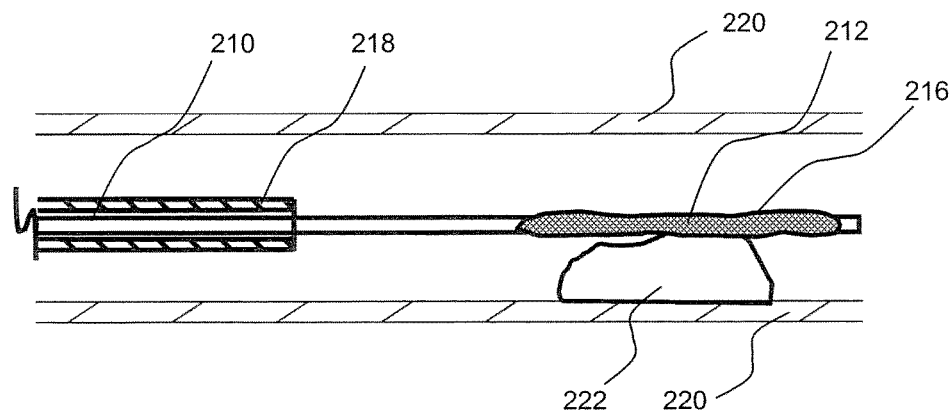
FIG. 2B is a side view illustration of an amphiphilic polymer coating disposed on an outer surface of unexpanded balloon of a balloon catheter adjacent to the focal area of local therapeutic agent delivery within a body lumen.
Figure 2C:
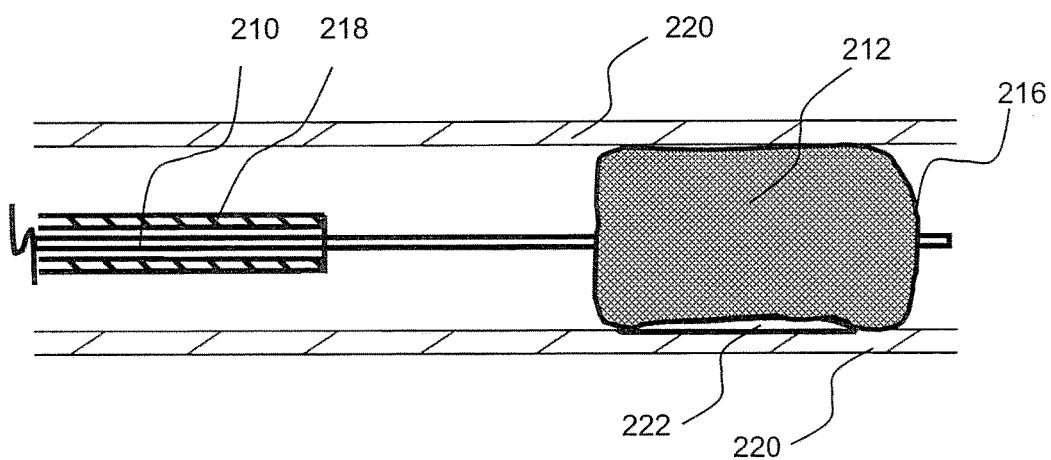
FIG. 2C is a side view illustration of the interface of the amphiphilic polymer coating disposed on an outer surface of an expanded balloon of a balloon catheter and the focal area of local therapeutic agent delivery within a body lumen.

FIG. 2A-FIG. 2C are illustrations of a particular embodiment in which the amphiphilic polymer coating comprising a therapeutic agent and amphiphilic polymer or co-polymer is locally delivered to the surface of a body lumen. As shown in FIG. 2A a balloon catheter 210 having an amphiphilic polymer coating 216 disposed on an unexpanded balloon 212 is provided and inserted into a body lumen 220. The catheter 210 may additionally include an optional protective sheath 218 over the unexpanded balloon 212 to prevent the amphiphilic polymer coating 216 from prematurely dissolving when the catheter is inserted into the body lumen 220. In an embodiment, the body lumen 220 may be an artery including a focal area 222, such as an unperturbed primary atherosclerotic or restenotic lesion. In an embodiment, the body lumen 220 may be a common bile duct or a branch of a common bile duct and focal area 222 is an intraluminal tumor.

As shown in FIG. 2B, the unexpanded balloon 212 is positioned adjacent the focal area 222 and the protective sheath 218 is retracted. The balloon 212 is then expanded (by inflation or otherwise) to contact the amphiphilic polymer coating 216 on the expanded balloon 212 against the body lumen 220 where the focal area 222 exists. In an embodiment, the expanded balloon 212 is a balloon catheter and the balloon is expanded to 2-20 atmospheres. Being amphiphilic, the coating 216 dissolves immediately when exposed to aqueous fluids such as blood in vivo. In an embodiment, at least 50%, by volume, of the amphiphilic polymer coating is removed from the balloon within 180 seconds of inflating in vivo. In an embodiment, at least 90%, by volume, of the amphiphilic polymer coating 216 is removed from the balloon within 300 seconds of inflating. In an embodiment, at least 90%, by volume, of the amphiphilic polymer coating 216 is removed from the balloon within a shorter amount of time such as 180 seconds, or 90 seconds of inflating in vivo depending upon the particular formulation.

In clinical use for angioplasty, it may be preferable for the balloon 212 to be expanded for only 5 to 300 seconds in a touch and go procedure. This time limitation is due to the type of medical procedure because a longer use time with the balloon inflated could result in focal or adjacent tissue damage that is deleterious to the therapeutic intent of the procedure. This damage could result from mechanical pressure and/or metabolic insufficiency caused by sustained inflation of the balloon including but not limited to tissue architecture, tissue inflammation, cell death, and induction of reactive scarring within the organ. In an embodiment, a coated angioplasty balloon may be tracked to a target lesion using standard techniques, the optional protective sheath is retracted and the angioplasty balloon is inflated against an artery wall. Hydration of the coating occurs immediately and causes the therapeutic agent to release into tissue, the coating polymer or co-polymer to dissolve, and some of the amphiphilic polymer coating to transfer from the balloon to the artery wall. This paving acts as drug reservoir and is transient. The significant or total solubility of the polymer or co-polymer in blood prevents embolic hazards associated with the coating. Also, this active dissolution of the polymer or co-polymer matrix assists the transfer of hydrophobic and substantially water-insoluble therapeutic agents such as paclitaxel from the balloon to the tissue. In accordance with embodiments of the invention, a significant portion of the therapeutic agent contained in the coating may be transferred to the tissue of the surrounding lumen during the procedure. In an embodiment, at least 5% of the therapeutic agent contained in the coating is imparted into the tissue of a vascular lumen within one hour of the touch and go procedure. In an embodiment, at least 25% of the therapeutic agent contained in the coating is imparted into the tissue of a vascular lumen within one hour of the touch and go procedure.

Several embodiments of the invention are described below with reference to the following non-limiting Examples regarding coating of PET and Nylon 12 coupons. Solution percentages provided are by weight.

Example 1

One (1.0) grams of a 7.5% solution of 60 K Dalton HPC in ethanol is mixed with 0.15 grams of 1% solution of propylene glycol (plasticizer) in acetone, 0.075 grams paclitaxel and 0.08 grams n-butanol. The mixture is heated in a water bath to dissolve the paclitaxel; a clear solution results. When dip coated (single dip) on PET coupons at a dip speed of about 10 inches/minute, and dried at room temperature, there results a slightly milky dry coating. About 3 $cm^2$ of coupon surface is coated per coupon. The average coating density determined by gravimetric analysis is 6 $\mu g/mm^2$ and the implied paclitaxel density is 3 $\mu g/mm^2$. The dry coating is sufficiently ductile to withstand a 180 degree bend without cracking or delaminating.

A coupon coated as above is immersed in 3 ml of 37° C. water for 3 minutes with agitation, after which the coupon is removed and the turbid suspension diluted with 9 ml dimethyl sulfoxide (DMSO) to produce a clear solution. Quantitative UV analysis at 260 nm and 280 nm vs. a standard curve shows an 88% recovery. This result demonstrates the rapid dissolution of the amphiphilic polymer coating and drug release in vitro. The in vivo milieu is expected to present serum proteins with a surfactant effect, which will increase the dissolution rate of the drug and coating polymer in vivo.

Example 2

0.075 grams paclitaxel is mixed with 0.9 grams of a 20% povidone-iodine solution in 2-propanol, 0.06 grams of a 10% propylene glycol solution in 2-propanol and 0.04 grams acetone. When dip coated (single dip) on a PET coupon at a dip speed of 10 inches/min, and dried at room temperature, there results a clear amber dry coating. About 2.5 µg/mm$^2$ of paclitaxel is deposited.

The above coupon is immersed in 1.5 ml of 37° C. water for 30 seconds. All of the coating dissolves in the water, and the solution is totally transparent amber, and not turbid as in Example 1.

Example 3

An identical formula to Example 2 is made, however non-iodinated PVP is employed instead of povidone-iodine of the same molecular weight (40 K Dalton). When dip coated (single dip) on a PET coupon at a dip speed of 10 inches/min, and dried at room temperature, there results a clear water white dry coating. About 2.5 µg/mm$^2$ of paclitaxel is deposited.

This coupon is immersed in 1.5 ml of 37° C. water for 30 seconds. All of the coating polymer dissolves in the water, and the solution shows a suspension of needle crystals. This suspension becomes more turbid after 24 hours, while the above amber solution from Example 2 remains transparent. This demonstrates that the povidone-iodine changes the aqueous solubility of paclitaxel.

Example 4

0.1 grams rapamycin (available from LC Laboratories, Woburn, Mass.) is dissolved in 0.08 grams of a 10% propylene glycol solution in 2-propanol and 0.053 grams acetone at 40° C. The solution is cooled to room temperature, then added to 1.2 grams of a 20% solution of povidone-iodine in 2-propanol. The formula is dip coated (single dip) on a Nylon 12 coupon, and dried at room temperature for 30 minutes. The above coupon is immersed in 1 ml of 37° C. water for one minute. All of the coating dissolves in the water, and the solution is clear amber.

Example 5

An identical formula to Example 4 is made, however non-iodinated C-30 PVP is employed instead of povidone-iodine. The formula is dip coated (single dip) on a Nylon 12 coupon, and dried at room temperature for 30 minutes. The above coupon is immersed in 1 ml of 37° C. water for one minute. All of the coating dissolves in the water, and the solution is turbid due to the water-insoluble rapamycin.

Example 6

0.1 grams everolimus (available from LC Laboratories, Woburn, Mass.) is dissolved in 0.08 grams of a 10% propylene glycol solution in 2-propanol and 0.053 grams acetone at 40° C. The solution is cooled to room temperature, then added to 1.2 grams of a 20% solution of povidone-iodine in 2-propanol. The formula is dip coated (single dip) on a Nylon 12 coupon, and dried at room temperature for 30 minutes. The above coupon is immersed in 1 ml of 37° C. water for one minute. All of the coating dissolves in the water, and the solution is clear amber.

Example 7

An identical formula to Example 6 is made, however non-iodinated C-30 PVP is employed instead of povidone-iodine. The formula is dip coated (single dip) on a Nylon 12 coupon, and dried at room temperature for 30 minutes. The above coupon is immersed in 1 ml of 37° C. water for one minute. All of the coating dissolves in the water, and the solution is turbid due to the water-insoluble everolimus.

Light scattering experiments at 600 nm and 700 nm were performed comparing the drug (paclitaxel, rapamycin and eyerolimus) and polymer eluted water solutions of Examples 2, 4 and 6 (containing povidone-iodine) with Examples 3, 5 and 7 (containing non-iodinated PVP). The results shown in Table I below provide a quite unexpected increase in solubility of paclitaxel, rapamycin and everolimus in the povidone-iodine eluted water solutions of Examples 2, 4 and 6 compared to the non-iodinated PVP eluted water solution of Examples 3, 5 and 7. Consequently, and quite unexpectedly this suggests that the iodine complexed PVP polymer may assist in tissue uptake of the non-aqueous soluble therapeutic agents in vivo.

TABLE I

Optical density measurements

| Example | Therapeutic Agent | Wavelength | Polymer | Optical Density | Solubility Increase |
|---|---|---|---|---|---|
| 2 | paclitaxel | 600 nm | PVP-iodinated | 0.120 | 2.99 |
| 3 | paclitaxel | 600 nm | PVP (non-iodinated) | 0.359 | — |
| 4 | rapamycin | 600 nm | PVP-iodinated | 0.079 | 3.10 |
| 5 | rapamycin | 600 nm | PVP (non-iodinated) | 0.245 | — |
| 6 | everolimus | 600 nm | PVP-iodinated | 0.068 | 2.38 |
| 7 | everolimus | 600 nm | PVP (non-iodinated) | 0.162 | — |
| 2 | paclitaxel | 700 nm | PVP-iodinated | 0.089 | 3.19 |
| 3 | paclitaxel | 700 nm | PVP (non-iodinated) | 0.284 | — |
| 4 | rapamycin | 700 nm | PVP-iodinated | 0.056 | 3.66 |
| 5 | rapamycin | 700 nm | PVP (non-iodinated) | 0.205 | — |
| 6 | everolimus | 700 nm | PVP-iodinated | 0.051 | 2.66 |
| 7 | everolimus | 700 nm | PVP (non-iodinated) | 0.136 | — |

Several embodiments of the invention are described below with reference to the following non-limiting Examples regarding coating of Nylon 12 coupons. Solution percentages provided are by weight.

Example 8

0.2 grams of iodine (Sigma-Aldrich) was added to 10 grams of methanol and dissolved with heat and agitation. 4.29 grams of PEG (4 K Daltons, Fluka) was then added, and dissolved with mild heat and agitation. 0.20 grams of paclitaxel was added to 1.66 grams of the above PEG-iodine solution. Mild heat and agitation were used to dissolve the paclitaxel.

A Nylon 12 coupon was coated with the formulation and dried for about 1 hour. The coupon was then soaked in 1.5 ml bovine serum at 37° C. for 3 minutes. 200 micro-liters of the serum sample was tested for optical density at 600 and 700 nm on a plate reader.

Example 9

An identical formula to Example 8 is made without iodine as a counter example. A Nylon 12 coupon was coated with the formulation and dried for about 1 hour. The coupon was then soaked in 1.5 ml bovine serum at 37° C. for 3 minutes. 200 micro-liters of the serum sample was tested for optical density at 600 and 700 nm on a plate reader.

Light scattering experiments at 600 nm and 700 nm were performed comparing the drug (paclitaxel) and polymer eluted bovine serum solutions of Example 8 (iodinated PEG) with Example 9 (non-iodinated PEG). The results shown in Table II below provide a quite unexpected increase in solubility of paclitaxel in the PEG eluted bovine serum solution of Example 8 compared to the non-iodinated PEG eluted bovine serum solution of Example 9. Consequently, and quite unexpectedly this suggests that the iodine complexed PEG polymer may assist in tissue uptake of the non-aqueous soluble therapeutic agents in vivo.

TABLE II

Optical density measurements

| Example | Therapeutic Agent | Wavelength | Polymer | Optical Density | Solubility Increase |
|---|---|---|---|---|---|
| Serum blank | — | 600 nm | — | 0.099 | — |
| 8 | paclitaxel | 600 nm | PEG-4KD-iodinated | 0.109 | 1.13 |
| 9 | paclitaxel | 600 nm | PEG-4KD-(non-iodinated) | 0.123 | — |
| Serum blank | — | 700 nm | — | 0.062 | — |
| 8 | paclitaxel | 700 nm | PEG-4KD-iodinated | 0.069 | 1.26 |
| 9 | paclitaxel | 700 nm | PEG-4KD-(non-iodinated) | 0.087 | — |

Example 10

A morphaline based initiator (ME-Br) was synthesized according to the following procedure. 18 ml 4-(2-hydroxyethyl) morpholine was dissolved in 200 ml toluene. 21.2 ml triethylamine (dried over $Na_2SO_4$) was added. The mixture was cooled in an ice bath. With stirring, 18.36 ml 2-bromoisobutyryl bromide was added dropwise over 30 minutes. The mixture was stirred in a cooling bath for an additional hour and then room temperature for 40 hours. The precipitated triethylammonium salt was filtered off and washed with 50 ml toluene. The solvent was rotoevaporated from the combined solution. The product, a brownish oil, was analyzed by NMR and was found to be highly pure. It was used without further purification.

A 10 KD polymer was synthesized according to the following ATRP procedure utilizing the ME-Br initiator. 4.076 grams of the above ME-Br initiator was loaded in a 100 ml round bottomed flask, equipped with a stir bar. A solution of 0.0280 grams tris[(2-pyridylmethyl]amine (TPMA), 0.0215 $CuBr_2$ and 0.0795 grams azobisisobutyronitrile (AIBN) in 100 ml ethanol was prepared and added. To this solution, 100 ml HEMA was added, the flask was capped, cooled in an ice bath and purged with nitrogen for 2 hours. The reaction was then carried out at 60° C. for 3 hours. 30% conversion was achieved. The polymer was precipitated in ether, washed with ether and dried. Molecular weight by GPC was 10,000 grams per mole. The 10 KD material was found to be water insoluble.

Example 11

A morphaline based initiator (ME-Br) was synthesized according to the procedure described in Example 10. A 7 KD polymer was synthesized according to the following procedure. 12.24 grams of the above ME-Br initiator was loaded in a 100 ml round bottomed flask, equipped with a stir bar. A solution of 0.0280 grams tris[(2-pyridyl)methyl]amine (TPMA), 0.0215 $CuBr_2$ and 0.0795 grams azobisisobutyronitrile (AIBN) in 100 ml ethanol was prepared and added. To this solution, 100 ml HEMA was added, the flask was capped, cooled in an ice bath and purged with nitrogen for 2 hours. The reaction was then carried out at 60° C. for 2 hours. 32% conversion was achieved. The polymer was precipitated in ether, washed with ether, redissolved in methanol, reprecipitated in ether and dried. Molecular weight by GPC was 7,000 grams per mole. The 7 KD material was found to have water solubility.

Example 12

A 30% solution of 7 KD poly(HEMA) in 2-propanol was prepared in accordance with the procedures of Example 11.

To 0.79 grams of this solution was added: 0.12 grams of 10% propylene glycol in 2-propanol, 0.06 grams acetone and 0.1 grams paclitaxel. Gentle heating was used to form a clear solution. This paclitaxel containing solution was used to dip coat onto Nylon 12 coupons. The coupons were dried at room temperature. The resultant coating was clear and free of obvious phase separation.

Example 13

A 30% solution of 7 KD poly(HEMA) in 2-propanol was prepared in accordance with the procedures of Example 11 with the addition of iodine at a level of 7% iodine based on poly(HEMA). A clear amber solution resulted. To 0.79 grams of this solution was added: 0.12 grams of 10% propylene glycol in 2-propanol, 0.06 grams acetone and 0.1 grams paclitaxel. Gentle heating was used to form an amber solution. This paclitaxel containing solution was used to dip coat onto Nylon 12 coupons. The coupons were dried at room temperature. The resultant coating was clear amber and free of obvious phase separation.

The coupons from Examples 12 and 13 were then immersed and agitated in 1.5 ml of adult bovine serum at 37° C. for 3 minutes. Subsequent gravimetric analysis showed that 90% of both coatings were removed by this process. 200 micro-liters of the serum samples were tested for optical density at 600 and 700 nm on a plate reader. The results are provided in Table III below, show an increase in solubility of paclitaxel in the iodinated poly(HEMA) eluted bovine serum solution of Example 13 compared to the non-iodinated poly(HEMA) eluted bovine serum solution of Example 12. Consequently, this suggests that iodine enhances the solubility of hydrophobic materials contained in the coating when in contact with biological systems. The data in Table III also indicates that poly(HEMA) synthesized using the ATRP initiator (ME-Br) forms a fully amphiphilic coating that achieves water solubility, and consequent rapid release of the drug; that poly(HEMA) is capable of complexing with iodine, resulting in improved solubility of a substantially water-insoluble, hydrophobic drug such as paclitaxel; that poly(HEMA) synthesized using the ATRP initiator (ME-Br) is useful as a medical device coating for rapid release of drug agents into tissue; and the addition of iodine to poly(HEMA) may enhance solubility and tissue uptake of a substantially water-insoluble, hydrophobic drug such as paclitaxel.

TABLE III

Optical density measurements

| Example | Therapeutic Agent | Wavelength | Polymer | Optical Density | Solubility Increase |
|---|---|---|---|---|---|
| Serum blank | — | 600 nm | — | 0.144 | — |
| 11 | paclitaxel | 600 nm | poly(HEMA)-7KD-iodinated | 0.150 | 1.09 |
| 10 | paclitaxel | 600 nm | poly(HEMA)-7KD (non-iodinated) | 0.163 | — |
| Serum blank | — | 700 nm | — | 0.102 | — |
| 11 | paclitaxel | 700 nm | poly(HEMA)-7KD-iodinated | 0.107 | 1.10 |
| 10 | paclitaxel | 700 nm | poly(HEMA)-7KD (non-iodinated) | 0.118 | — |

Clinical Study 1

0.1 grams paclitaxel was dissolved in 0.1 grams ethanol and 0.18 grams of 50% PEG-400 in acetone at 45° C. The solution was then cooled to room temperature and added to 0.55 grams of 20% povidone-iodine in 2-propanol. The resulting coating solution contained a D/P ratio of 50%, 31.8 wt % non-volatile components, with the paclitaxel representing 33.3 wt % of the non-volatile components.

Two 2.0×20 over-the-wire balloon catheters (available from ev3 Inc., Plymouth, Minn.) were inflated and cleaned by sonication in 2-propanol for 30 seconds. The catheters were then dried at room temperature and plasma treated for 18 seconds in an argon atmosphere while the balloons were rotated at 0.17 in/min. The balloons were dipped into the resulting coating solution and extracted at a 30 degree angle from horizontal, while rotating the balloon at 30 rpm. When dried, the amount of dried coatings on the balloons was about 1.1-1.2 mg. The first balloon was extracted at 0.17 in/min, resulting in an approximate paclitaxel density of 2.8 $\mu g/mm^2$ on the balloon surface when dried. The second balloon was extracted at 0.15 in/min, resulting in a drug density of 2.4 $\mu g/mm^2$ on the balloon surface when dried. Efficacy of the paclitaxel tissue uptake was tested in vivo in three New Zealand white rabbits. Carotid and femoral arteries were exposed via cut downs, and the catheters were inserted directly into the artery segments, inflated to nominal diameter for 60 seconds, then deflated and removed. The treated artery segments were removed at 40 minutes post deflation and stored immediately on dry ice. Subsequent analysis by liquid chromatography-mass spectrometry (LC/MS) for paclitaxel showed that the average drug concentration in the tissue for the first balloon was 500 µg paclitaxel/gram tissue, and 381 µg paclitaxel/gram tissue for the second balloon.

Clinical Study 2

An iodinated-PEG solution with paclitaxel was prepared as described in Example 8, except that the molecular weight of PEG used was 10 K Daltons (Fluka). Three 2.5×20 over-the-wire balloon catheters (ev3, Inc.) were inflated and cleaned by sonication in 2-propanol for 30 seconds. The catheters were dried at room temperature and subsequently plasma treated for 18 seconds in an atmospheric argon plasma while the balloons were rotated at 30 rpm in the plasma jet. The balloons were then dipped into the coating solution and extracted. When dried, the amount of dried coating on the balloons was about 1.8 mg to 1.9 mg, approximating a drug density of 3 $\mu g/mm^2$ on the balloon surface. The dried catheters were sheathed.

Efficacy of the paclitaxel tissue uptake was texted in vivo in three New Zealand white rabbits. Carotid and femoral arteries were exposed via cut downs, and the catheters were inserted directly into the artery segments, inflated to nominal diameter for 60 seconds, then deflated and removed. The treated artery segments were removed at 40 minutes post deflation and stored immediately on dry ice. Subsequent analysis by LC/MS for paclitaxel showed that the average drug concentration in tissue was 867 µg/g (µ gram drug/gram tissue).

In both clinical studies the amount of average paclitaxel uptake by the tissue was greater than data provided in the SeQuent® Please product brochure number 6050120 (available from B. Braun Vascular Systems, Berlin, Germany) where a tissue concentration of approximately 325 µg paclitaxel/gram tissue was reported in porcine coronary arteries at roughly the same time period (approximately 40 minutes) post deflation in which a paclitaxel drug loading of 3 $\mu g/mm^2$ in a polymer-free coating was utilized.

Diseases of the Vasculature

One therapeutic area where embodiments of the present invention will be applicable is the treatment of luminal disorders of the vasculature. In general, luminal disorders may be classified as native (atherosclerotic, thromboembolic) or iatrogenic (restenosis) diseases. These luminal disorders may include but not be limited to atherosclerosis, atheromatous lesions, vulnerable plaque, thromboembolic obstructions, vascular graft disease, arteriovenous fistula disease, arteriovenous graft disease and restenosis.

Atherosclerosis is a complex disease of the vessel wall involving the interplay of inflammation, proliferation, lipid deposition and thrombus formation. Atherosclerosis promotes the formation of atheromatous plaques that may progress slowly over several years, leading to progressive obstruction of the vessel lumen manifesting clinically as angina. Atheromatous plaques, may also become "vulnerable plaques" due to an unstable collection of white blood cells (primarily macrophages) and lipids (including cholesterol) in the wall of an artery and become particularly prone to rupture. A rupture of a vulnerable plaque is commonly believed to be the cause of sudden thrombotic obstructions of the vessel lumen due to the rapid formation of blood clots at the rupture site, leading to the clinical manifestations of heart attack or stroke. Vulnerable plaques may not significantly obstruct a vessel lumen until rupture, thus they are pre-obstructive lesions. It is envisioned that a desirable therapeutic target is the prevention of obstruction of the vessel lumen by the treatment of vulnerable plaques prior to their rupture. Specifically, embodiments of the present invention could be applied to a catheter with a tip that is expandable to allow uniform and complete contact with and delivery of therapeutic agents to sites of luminal atheromatous or vulnerable plaques. The local delivery of therapeutic agents would enable a much higher, targeted, local concentration of said agents than might otherwise be achieved by systemic delivery. Moreover, a local delivery strategy would enable the use of therapeutic agents that otherwise may be poor candidates for systemic delivery due to lack of bioavailability and/or undesirable or toxic side effects at concentrations needed to achieve efficacy.

Restenosis

One therapeutic area where embodiments of the present invention will be applicable is inhibiting the process of restenosis. Restenosis is the result of a complex process involving inflammation and proliferation activated by a response to a percutaneous or surgical vascular intervention. Examples of these percutaneous or surgical interventions may include but are not limited to the revascularization of vascular bypass grafts, arteriovenous fistulas, arteriovenous grafts and percutaneous revascularization of coronary, femoral, and carotid vessels. Atherosclerotic plaque arising from the arterial wall can reduce cross-sectional flow area which limits flow to downstream organs. Cross-sectional flow area can be restored by displacing (e.g. expandable balloon or stent) or removing the lesion (e.g. directional or rotational atherectomy). In the months to weeks after revascularization local proliferative of arterial wall smooth muscle cells can create an obstruction to flow at the site of the original atherosclerotic plaque. Paclitaxel is a diterpene molecule containing a complex taxane ring that inhibits cytokinesis by promoting microtubule polymerization. Paclitaxel inhibits smooth muscle cell proliferation and restenosis after balloon angioplasty in a mammalian arteries. Paclitaxel inhibits restenosis after percutaneous coronary revascularization in humans when it is delivered over days to weeks from implanted metal stents that were retained after the revascularization procedure. Brief exposure to paclitaxel (20 minutes or less) can inhibit smooth muscle cell proliferation for sustained periods (14 days). Clinical studies demonstrate that paclitaxel can also effectively inhibit restenosis after femoral and coronary revascularization when it is delivered over a short period (minutes) from an expandable balloon coated with the drug.

Restenosis is a complex molecular process that involves both smooth muscle cell proliferation in addition to inflammatory processes. Dexamethasone is a glucocorticoid that reduces inflammation and restenosis after balloon angioplasty in a mammalian arteries. This suggests that there may be clinical benefit in delivering antimitotic agents such as paclitaxel in combination with anti-inflammatory agents such as dexamethasone from an expandable balloon coated with the two therapeutic agents.

Pulmonary Disease

Another therapeutic area where embodiments of the present invention could be applicable is a luminal surface of normal or diseased airway for the treatment or prevention of focal diseases of the lung and airways. This embodiment may be used in conjunction with both a rigid or flexible bronchoscope which are commonly used to facilitate access to and visualization of the target treatment area.

In general, focal diseases of the airways area neoplasms that are categorized as either benign or malignant. Primary neoplasms may be classified as epithelial, mesenchymal or lymphoid tumors; more than 20 types of tracheal neoplasms have been described.

Carcinoid tumors represent approximately 85 percent of adenomas of the tracheobronchial tree. Adenoid cystic carcinoma is the most frequent adenoma of the trachea. Adenoid cystic carcinoma (or cylindroma) is the second most common malignancy and also the second most common primary tracheal neoplasm.

Conventional treatment for lung cancer can involve surgical removal of tumor, chemotherapy, or radiation therapy, as well as combinations of these methods. The decision about which treatments will be appropriate take into account the localization and extent of the tumor as well as the overall health status of the patient. An example of adjuvant therapy is chemotherapy or radiotherapy administered after surgical removal of a tumor in order to be certain that all tumor cells are killed.

Depending upon the specific neoplasm type and behavior as well as the time of diagnosis, the neoplasm may or may not present a physical obstruction or protrusion into the lumen of the airways. It is envisioned that an approach to restoring functional luminal patency could be to mechanically restore luminal patency by displacing the tumor with a balloon or reduce tumor bulk and then locally delivering a drug to inhibit tumor growth and/or tumor survival. Local drug delivery using embodiments of the present invention could be an effective method of delivering chemotherapeutic agents effective against benign or malignant neoplasms to the luminal aspect of the tumor. Specifically, embodiments of the present invention could be applied to a catheter or a bronchoscope and advanced antegradely or retrogradely to the intended site of local drug delivery. It is envisioned that embodiments of the present invention will enable the local delivery of bioactive (therapeutic) agents to the surface of normal or diseased airway lumens and may be used singly or in combination with surgical removal, chemotherapy and radiation therapy. The local delivery of therapeutic agents would enable a much higher, targeted, local concentration of said agents than might otherwise be achieved by systemic delivery. Moreover, a local delivery strategy would enable the use of therapeutic agents that otherwise may be poor candidates for systemic delivery due to lack of bioavailability and/or undesirable or toxic side effects at concentrations needed to achieve efficacy. The targeted local delivery of therapeutic agents may be used to reduce tumor size to facilitate surgical removal and may eliminate the need for and/or reduce the duration or intensity of systemic chemotherapy or radiotherapy which have numerous unpleasant side effects.

Gastrointestinal Disease

Another therapeutic area where embodiments of the present invention could be applicable is gastrointestinal disease including, but limited to, benign and malignant tumors of the esophagus, biliary tract, colon, and small bowel.

Esophageal tumors are caused by dysregulated division of esophageal smooth muscle or epithelial cells. The tumors can be either benign (e.g. leiomyoma) or malignant (squamous cell carcinoma or adenocarcinoma). These tumors can grow into the lumen and compromise the functional cross-sectional area of the esophagus causing dysphagia (abnormal swallowing) and consequent malnutrition.

It is envisioned that an approach to restoring functional luminal patency could be to mechanically restore luminal patency by displacing the tumor with a balloon or metal dilator or reduce tumor bulk (e.g. laser ablation), and then locally delivering a therapeutic agent to inhibit tumor growth and/or tumor survival. Local therapeutic agent delivery using embodiments of the present invention could be an effective method of delivering chemotherapeutic agents effective against benign or malignant esophageal tumors to the luminal aspect of the tumor. Specifically, embodiments of the present invention could be applied to a catheter or an endoscope and advanced antegradely or retrogradely to the intended site of local drug delivery. Chemotherapeutic agents that could be effective in this manner include, but are not limited to, microtubule stabilizing agents (e.g. taxanes including paclitaxel and epothilones), topoisomerase I inhibitors (e.g. irinotecan), platinum derivatives (e.g. oxaliplatin, cisplatin, carboplatin), anthracyclines (daunorubicin, epirubicin), 5-FU, and targeted biologic therapies (e.g. anti-VEGF antibodies such as bevacizumab). The advantages of this method are that high doses of effective chemotherapeutic agents can be delivered to the tumor without systemic toxicity, the patient's diet would not have to be modified to prevent food impaction, and the mechanical complications of stent placement including indirect tracheal compression, stent migration, and stent occlusion could be avoided. Therapeutic agent for the above indication that exhibit water-only solubility or require water for solubilization such as carboplatin, cisplatin, the epothilones, and targeted proteins such as antibodies (such as the anti-VEGF antibody bevacizumab) can be formulated into the disclosed amphiphilic polymer coating by the use of water as part or all of the solvent.

A similar approach could be used with malignancies of the biliary tract. Cholangiocarcinoma is the most common biliary tract malignancy. It is caused by dysregulated division of cholangiocytes. These tumors can compromise the functional lumen of the intra- or extra-hepatic biliary tree causing cholestasis and consequent cholangitis, pruritis, fat malabsorption, and anorexia.

It is envisioned that an approach to restoring functional luminal patency could be to mechanically restore luminal patency by displacing the tumor with a balloon, blade, or metal dilator or reduce tumor bulk (e.g. laser ablation), and then locally deliver a therapeutic agent to inhibit tumor growth and/or tumor survival utilizing embodiment of the present invention. Chemotherapeutic agents that could be effective in this manner include, but are not limited to, microtubule stabilizing agents (e.g. taxanes including paclitaxel and epothilones), platinum derivatives (e.g. oxaliplatin, cisplatin, carboplatin), anthracyclines (daunorubicin, epirubicin), 5-FU, DNA cross-linkers (mitomycin-C), alkylating nitrosoureas (lomustine), interferons (interferon-alpha), and targeted biologically active agents (e.g. EGFR inhibitors such as cetuximax). The advantages of this method are that high doses of effective chemotherapeutic agents can be delivered to the tumor without systemic toxicity, and the mechanical complications of stent placement including stent migration and stent occlusion could be avoided.

Approaches similar to that described above for esophageal and biliary tract malignancies could be developed for small bowel and colonic malignancies. Analogous approaches could also be used to locally delivery therapeutic agents to non-malignant gastrointestinal diseases (e.g. anti-inflammatory agents delivered to treat inflammatory bowel disease). Therapeutic agents for the above indication that exhibit water-only solubility or require water for solubilization such as carboplatin, cisplatin, the epothilones, interferons (interferon-alpha) and targeted proteins such as antibodies (such as the EGFR inhibitor cetuximab) can be formulated into the disclosed amphiphilic polymer coating by the use of water as part or all of the solvent system.

In the foregoing specification, various embodiments of the invention have been described. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A catheter assembly comprising:
   an expandable structure having an outer surface;
   a non-durable coating disposed on the outer surface of the expandable structure, the non-durable coating including a plasticizer in combination with poly(hydroxyethyl methacrylic) acid complexed with iodine; and
   a substantially water-insoluble therapeutic agent dispersed in the non-durable coating.

2. The catheter assembly of claim 1, wherein the plasticizer includes propylene glycol, triethyl citrate, glycerol, or dibutyl sebacate.

3. The catheter assembly of claim 1, wherein the poly(hydroxyethyl methacrylic) acid has a number average molecular weight below 8 KD.

4. The catheter assembly of claim 1, wherein the poly(hydroxyethyl methacrylic) acid is co-polymerized with a monomer including glycidyl methacrylate or acrylic acid.

5. The catheter assembly of claim 1, wherein the substantially water-insoluble therapeutic agent includes anti-proliferative agents, anti-platelet agents, anti-inflammatory agents, anti-thrombotic agents, or thrombolytic agents.

6. The catheter assembly of claim 1, wherein the substantially water-insoluble therapeutic agent is paclitaxel.

7. A catheter assembly comprising:
   an expandable structure having an outer surface;
   a non-durable coating disposed on the outer surface of the expandable structure, the non-durable coating including a plasticizer in combination with poly(hydroxyethyl methacrylic) acid; and
   a substantially water-insoluble therapeutic agent and non-covalently bound iodine dispersed throughout the non-durable coating.

8. The catheter assembly of claim 7, wherein the plasticizer includes propylene glycol, triethyl citrate, glycerol, or dibutyl sebacate.

9. The catheter assembly of claim 7, wherein the poly (hydroxyethyl methacrylic) acid has a number average molecular weight below 8 KD.

10. The catheter assembly of claim 7, wherein the poly (hydroxyethyl methacrylic) acid is co-polymerized with a monomer including glycidyl methacrylate or acrylic acid.

11. The catheter assembly of claim 7, wherein the substantially water-insoluble therapeutic agent includes anti-proliferative agents, anti-platelet agents, anti-inflammatory agents, anti-thrombotic agents, or thrombolytic agents.

12. The catheter assembly of claim 7, wherein the substantially water-insoluble therapeutic agent is paclitaxel.

* * * * *